United States Patent
Säll

(10) Patent No.: US 12,337,099 B2
(45) Date of Patent: Jun. 24, 2025

(54) NOZZLE AND CARTRIDGE ASSEMBLY

(71) Applicant: SHL MEDICAL AG, Zug (CH)

(72) Inventor: Daniel Säll, Segeltorp (SE)

(73) Assignee: SHL Medical AG, Zug (CH)

( * ) Notice: Subject to any disclaimer, the term of this patent is extended or adjusted under 35 U.S.C. 154(b) by 1090 days.

(21) Appl. No.: 17/054,924

(22) PCT Filed: May 27, 2019

(86) PCT No.: PCT/EP2019/063567
§ 371 (c)(1),
(2) Date: Nov. 12, 2020

(87) PCT Pub. No.: WO2019/228943
PCT Pub. Date: Dec. 5, 2019

(65) Prior Publication Data
US 2021/0213213 A1     Jul. 15, 2021

Related U.S. Application Data

(60) Provisional application No. 62/677,291, filed on May 29, 2018.

(51) Int. Cl.
*A61M 11/00* (2006.01)
*A61F 9/00* (2006.01)
(Continued)

(52) U.S. Cl.
CPC ......... *A61M 11/007* (2014.02); *A61F 9/0008* (2013.01); *A61M 11/00* (2013.01);
(Continued)

(58) Field of Classification Search
CPC ............. A61M 15/0065; A61M 11/007; A61M 5/285; A61M 2207/00; A61M 2205/073; A61M 2205/3375; A61M 2205/3317; A61M 2205/3389; A61M 15/0036; A61M 2205/3306; A61M 15/0035;
(Continued)

(56) References Cited

U.S. PATENT DOCUMENTS 6,068,198 A * 5/2000 Gupta .................. A61M 11/001
239/324
6,983,747 B2 * 1/2006 Gallem ............. A61M 15/0015
239/338
(Continued)

FOREIGN PATENT DOCUMENTS

CN   102196865 A   9/2011
WO   2013/064677 A1   5/2013
(Continued)

OTHER PUBLICATIONS

International Search Report and Written Opinion for Int. App. No. PCT/EP2019/063567, mailed Aug. 5, 2019.

*Primary Examiner* — Frederick C Nicolas
(74) *Attorney, Agent, or Firm* — McDonnell Boehnen Hulbert & Berghoff LLP

(57) ABSTRACT

An assembly for a spray device is presented where the assembly has a cartridge containing a liquid to be pressurised, and a micro nozzle configured to produce an aerosol from the pressurised liquid, wherein the micro nozzle is permanently attached to the cartridge.

18 Claims, 3 Drawing Sheets

(51) Int. Cl.
*B05B 11/02* (2023.01)
*A61M 11/06* (2006.01)
*A61M 15/00* (2006.01)
*B05B 1/14* (2006.01)
*B05B 15/65* (2018.01)

(52) U.S. Cl.
CPC ............ *B05B 11/02* (2013.01); *A61M 11/001* (2014.02); *A61M 11/06* (2013.01); *A61M 15/0021* (2014.02); *A61M 2207/00* (2013.01); *A61M 2209/045* (2013.01); *B05B 1/14* (2013.01); *B05B 15/65* (2018.02)

(58) Field of Classification Search
CPC ...... A61M 2205/071; A61M 2209/045; A61M 11/001; A61M 11/06; A61M 15/0021; A61M 11/00; B65B 3/003; B65B 3/30; B65B 7/28; B05B 11/0054; B05B 11/028; B05B 15/40; B05B 11/1091; B05B 17/0638; B05B 9/047; B05B 11/02; B05B 1/14; B05B 15/65; A61F 9/0008
See application file for complete search history.

(56) References Cited

U.S. PATENT DOCUMENTS

| | | | | |
|---|---|---|---|---|
| 2004/0094146 | A1* | 5/2004 | Schiewe | B05B 11/02 128/200.14 |
| 2015/0352298 | A1* | 12/2015 | Egerström | A61M 5/315 128/200.14 |
| 2016/0022928 | A1* | 1/2016 | Cheng | A61M 15/0025 128/200.14 |
| 2016/0082437 | A1* | 3/2016 | Perroud | B01L 3/502792 204/453 |
| 2017/0281880 | A1* | 10/2017 | Van Egmond | B05B 15/40 |

FOREIGN PATENT DOCUMENTS

| | | |
|---|---|---|
| WO | 2013/125555 A1 | 8/2013 |
| WO | 2014/111370 A1 | 7/2014 |
| WO | 2014/137215 A1 | 9/2014 |
| WO | 2015/194962 A1 | 12/2015 |

* cited by examiner

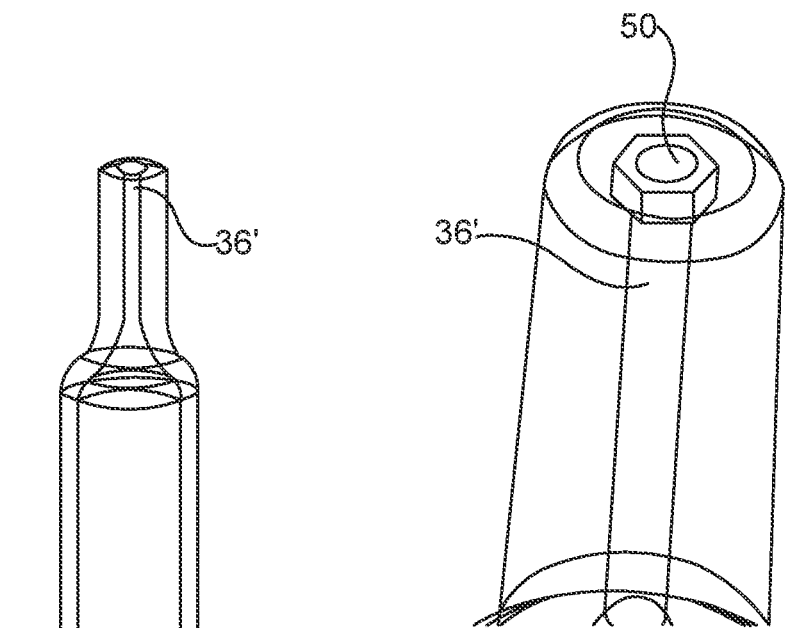
Fig. 2B
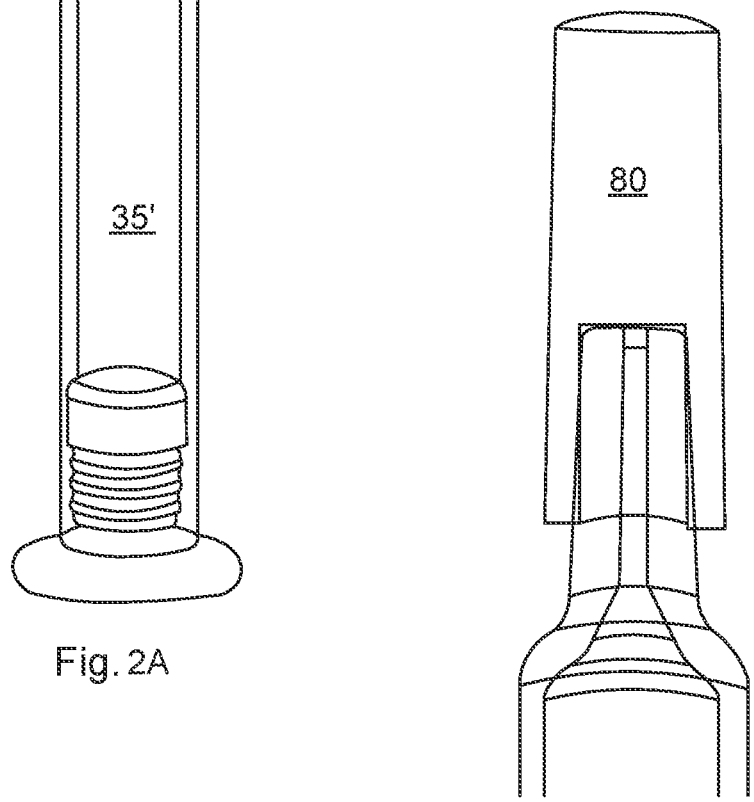
Fig. 2A
Fig. 2C

NOZZLE AND CARTRIDGE ASSEMBLY

CROSS REFERENCE TO RELATED APPLICATIONS

The present application is a U.S. National Phase Application pursuant to 35 U.S.C. § 371 of International Application No. PCT/EP2019/063567 filed May 27, 2019, which claims priority to U.S. Provisional Patent Application No. 62/677,291 filed May 29, 2018. The entire disclosure contents of these applications are herewith incorporated by reference into the present application.

TECHNICAL FIELD

The present disclosure relates to a spray nozzle unit assembled with a cartridge, and in particular to a micro spray nozzle unit assembled with a cartridge containing a liquid to be sprayed.

BACKGROUND

There are many different kinds of spray devices on the market today. Micro nozzle devices comprising micro nozzles form an increasingly important and growing segment of the market. Micro nozzles may for instance be found in ink jet printing appliances, 3D printers, perfume containers and medicament delivery devices. Often the containers, e.g. syringes or cartridges, are pre-assembled with the spray device or with a container holder of the spray device. When the contents of the container are spent, the user either has to throw away the whole spray device, or at least the container holder.

WO 2014/111370 discloses a medicament delivery device comprising a medicament container. A nebulising nozzle is arranged at the proximal end of the medicament container. The nebulising nozzle contains a chip with a plurality of micro channels capable of creating an aerosol of droplets of medicament. The nebulising nozzle is assembled with the medicament container holder.

SUMMARY

One drawback with the medicament delivery device disclosed in WO 2014/111370 is that it requires that the entire medicament container holder is replaced in case the medicament delivery device is to be reused.

It would be of interest to be able to assemble the nozzle with the container/cartridge so that the user may easily replace spent cartridges and nozzles in the spray device, without unnecessary waste.

In view of the above, an object of the present disclosure is to provide an assembly for a spray device which solves or at least mitigates problems of the prior art.

There is hence according to a first aspect of the present disclosure provided an assembly for a spray device, which assembly comprises: a cartridge containing a liquid to be pressurised, and a micro nozzle configured to produce an aerosol from the pressurised liquid, wherein the micro nozzle is permanently attached to the cartridge.

The cartridge together with the micro nozzle may thereby be discarded after use. As a result, it may not be required to replace a cartridge holder, but only the cartridge after the liquid contained in the cartridge has been dispensed.

One embodiment comprises a cartridge adapter configured to hold the micro nozzle in position relative to the cartridge.

According to one embodiment the cartridge is a syringe provided with a hole and the micro nozzle is positioned in the hole.

The syringe may be a standard syringe.

The syringe may for example be a plastic syringe or a glass syringe.

According to one embodiment the micro nozzle has a hexagonal shape which fits in the hole.

According to one embodiment the micro nozzle is arranged with a press fit in the hole and/or is glued to the syringe.

According to one embodiment the cartridge adapter is arranged with a press fit in the hole and/or glued to the syringe.

One embodiment comprises a boot arranged on a tip of the syringe, configured to hermetically protect the hole and the micro nozzle from contamination.

According to one embodiment the micro nozzle, the cartridge adapter, and the cartridge are integrated by moulding.

One embodiment comprises a crimp seal crimped to the cartridge, wherein the cartridge adapter and the micro nozzle cooperate with the crimp seal to be permanently attached to the cartridge.

According to one embodiment the cartridge is a medical cartridge.

There is according to a second aspect of the present disclosure provided a method of assembling an assembly for a spray device, wherein the method comprises: attaching a micro nozzle permanently to a cartridge before or in conjunction with filling the of the cartridge.

This ensures sterilisation of the assembly.

With the term "in conjunction" is meant just before or after the attachment of the micro nozzle. For example, this would mean that the assembly is not transported from one factory to another between the attachment of the micro nozzle and the filling. The two operations are generally performed in the same factory as subsequent or simultaneous operations.

One embodiment comprises placing a cartridge adapter and the micro nozzle in a moulding tool, and injecting plastic to mould the cartridge.

One embodiment comprises crimping a crimp seal to permanently attach the crimp seal, a cartridge adapter and the micro nozzle to the cartridge.

According to one embodiment the cartridge is a syringe, wherein the micro nozzle has a hexagonal shape, the method comprising attaching the micro nozzle into a hole of the syringe.

According to one embodiment the attaching involves press fitting the micro nozzle and/or gluing of the micro nozzle.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which:

FIG. 1A is a perspective view of an example of a dispenser unit of a spray device;

FIG. 2A is a perspective view of a syringe with a hole;

FIG. 2B is a perspective view of a tip of the syringe of FIG. 3A, comprising a cartridge adapter;

FIG. 2C is a perspective view of the tip of the syringe of FIG. 3A, comprising a boot;

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1A:
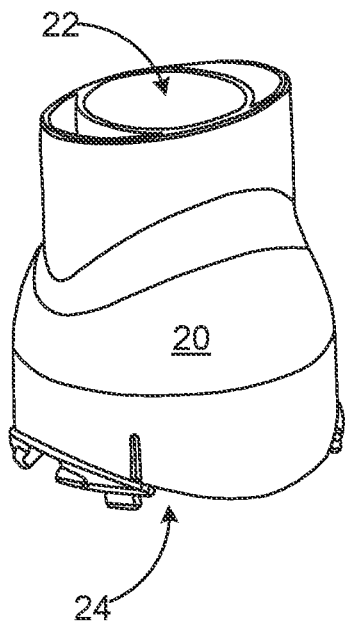
FIG. 1B is a cross-sectional view of a micro nozzle assembled with a dispenser unit and a cartridge for spray liquid.
FIG. 1C is a conceptual view of a proximally facing outlet side of a micro nozzle.
FIG. 1D is a conceptual view of a distally facing inlet side of a micro nozzle.

FIG. 1A shows a perspective view of an example of a dispenser unit 20 of a spray device. The dispenser unit 20 has proximal side 22, through which an aerosol is sprayed, and a distal side 24 which is mounted on a spray device. In this example, the dispenser unit 20 is a mouthpiece of an inhalation spray device, but many other types of dispenser units, for any applications requiring a very fine aerosol, are conceivable. Other examples include eye spray devices and perfume dispensers, to name but a few.

Figure 1C:
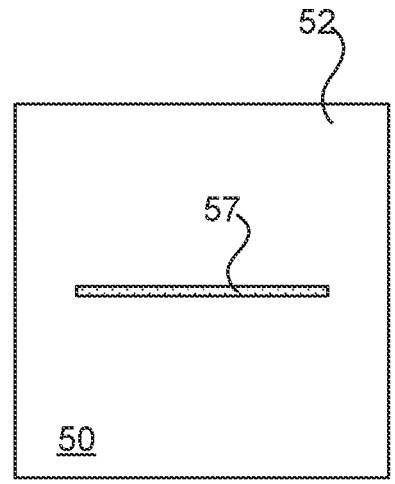
Figure 1B:
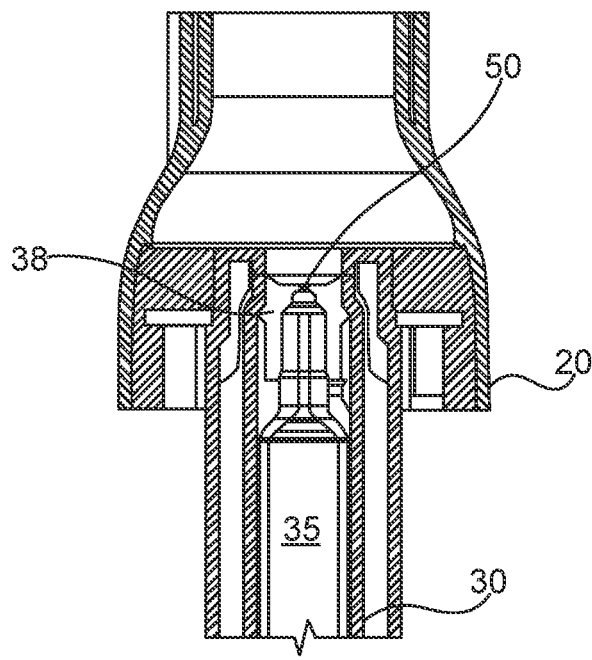

FIG. 1B shows a cross-sectional view of a dispenser unit 20 of a spray device. The dispenser unit 20 hence forms part of a spray device. The spray device may be a medicament delivery device, for example an inhaler or an eye dispenser. The spray device comprises a cartridge holder 30 and a cartridge 35. The cartridge holder 30 is configured to hold the cartridge 35. The cartridge 35 is filled with a liquid. The liquid may for example be a medicament. The spray device comprises a micro nozzle 50. The micro nozzle 50 may for example be a spray nozzle chip. The micro nozzle 50 is configured to create an aerosol as the liquid is dispensed from the cartridge 35. The micro nozzle 50 is permanently attached to the cartridge 35. The micro nozzle 50 is hence fixedly attached to the cartridge 35.

The cartridge 35 has a hole or orifice, through which the liquid may move when liquid is to be dispensed from the cartridge 35. The micro nozzle 50 is arranged such that the liquid must move through the micro nozzle 50 when the liquid flows through the hole to be dispensed from the cartridge 35.

The cartridge 35 is connected to the dispenser unit 20. When liquid is to be dispensed from the spray device, the liquid in the cartridge 35 is pressurised. The spray device may comprise a pressurising device, such as a plunger rod, which can be moved in the cartridge 35 to cause the liquid to be pushed through the micro nozzle 50 to form an aerosol. The aerosol is dispensed from the spray device via the dispenser unit 20.

The cartridge may for example be a container or a syringe. All three terms are herein defined as denoting a vessel containing a liquid.

The spray device may comprise a cartridge adapter. The cartridge adapter may be a micro nozzle carrier. The micro nozzle 50 may for example be mounted in the cartridge adapter or mounted onto the cartridge adapter. An example of a cartridge adapter is shown in FIG. 1B. The cartridge adapter 38 is arranged to hold the micro nozzle 50 in position relative to the cartridge 35 and relative to the dispenser unit 20. This applies to all examples disclosed herein. In FIG. 1B, the micro nozzle 50 is mounted in the cartridge adapter 38.

The cartridge adapter 38 may be fixed to the cartridge 35 when the cartridge is filled with liquid or prior to the cartridge 35 being filled with liquid. An end user may receive a plurality of cartridges 35 fitted with cartridge adapters 38 and micro nozzles 50. A cartridge 35 may then be placed in the spray device with the dispenser unit 20 when the spray device is to be used. The cartridge 35 may after use be replaced with an identical cartridge 35.

Figure 1D:
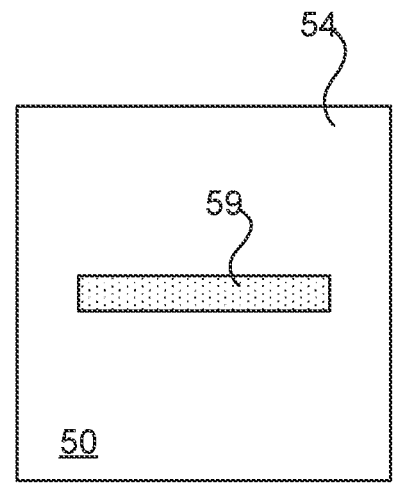

FIGS. 1C and 1D two opposite sides of the micro nozzle 50. The micro nozzle 50 has an inlet side 54 and an outlet side 52. The inlet side 54 is provided with inlet orifices 59. The inlet orifices 59 may be sieve orifice. The outlet side 52 is provided with outlet orifices 57. The outlet orifices 57 may be spray orifices. The inlet orifices 59 may be more in number than the outlet orifices 57. The inlet and outlet orifices are connected inside the micro nozzle 50 by cavities and/or channels.

In FIG. 1C, the orifices are symbolised by areas of dark dots. The outlet side 52 forms a proximal side of the micro nozzle 50. The inlet side 54 forms a distal side of the micro nozzle 50. The micro nozzle 50 may comprise a ceramic or a monocrystalline material, such as a semiconductor material, which is suitable for micro structure processing.

A micro nozzle is herein defined as a nozzle having orifice diameters between for example 0.5 μm and 10 μm, which may produce an aerosol of very fine droplets. The aerosol may be produced by pressurising a liquid on the inlet side 54 of the nozzle, which liquid is expelled as droplets at the outlet side 52 of the nozzle. Droplet diameters may be approximately 1 μm in the lower range of orifice diameters. Depending on viscosity, pressure and orifice diameters, the expelled liquid may form into Rayleigh droplet trains. The micro nozzle has at least one orifice on the inlet side and at least one orifice on the outlet side. The configuration of the channels and orifices are not essential in themselves for this disclosure. However, as shown in FIGS. 1C and 1D, it is customary to provide a larger number of orifices on the inlet side 54 than on the outlet side 52 because the orifices are normally formed in membranes which cover a cavity, or channel, in the micro nozzle. It is therefore preferable to have a smaller pressure drop on the inlet side 54 than on the outlet side 52.

According to one example, the cartridge is a syringe. The syringe may for example be a standard glass syringe or a standard plastic syringe. The micro nozzle is fixedly assembled with the syringe. If the syringe for example is a standard glass syringe, a standard and proven sheath 80, e.g. a needle shield, can be used as a sterile barrier. The sheath 80 may hence be assembled with the syringe 35' to act as a sterile barrier.

FIG. 2A shows a standard glass syringe 35'. The syringe 35' has a circular hole 36' for expelling its contents. In medical injection applications, a needle is fitted in such a hole. The hole 36' is typically circular with a diameter of approximately 1 mm. A micro nozzle 50 is typically around 1 mm$^2$. The micro nozzle 60 may have a square shape, when diced from a wafer.

According to one example, the micro nozzle 50 has a hexagonal shape. The micro nozzle 50 may hence be diced in a hexagonal shape. Stealth dicing (laser dicing) may for example be used for dicing the micro nozzle in a hexagonal shape. The hexagonal shape enables an area increase of 30% compared to a square shape. It also allows a better fit of the micro nozzle 50 in the round hole 36', as shown in FIG. 2B. The micro nozzle may according to one variation have a polygonal shape with a higher number of edges than six. The micro nozzle may for example have an octagonal shape.

The micro nozzle 50 may for example be fixedly arranged in the hole 36' by means of press fit and/or using an adhesive such as glue.

According to one example, the micro nozzle 50 may be attached to a cartridge adapter. The cartridge adapter 38 may for example be a carrier made of stainless steel. The cartridge adapter may subsequently be attached to a tip of the syringe 35' so that the micro nozzle 50 is positioned in the hole 36'. According to one variation, the cartridge adapter may have a hexagonal shape. Alternatively, the cartridge adapter may have a rectangular, for example a square shape, or a polygonal shape with for example more edges than six. The cartridge adapter could for example be octagonal. Alternatively, the cartridge adapter could have a round shape.

According to one variation the cartridge adapter is fixedly arranged in the hole 36' by means of press fit and/or using an adhesive such as glue.

Turning now to FIG. 2C, the spray device may furthermore comprise a boot such as a sheath. The boot may be placed on the top of the syringe 35' to provide hermetical sealing of the syringe 35'. During sterilisation, the boot, e.g. a sheath 80 such as a standard needle shield, may be hermetically placed on the tip of the syringe to protect the micro nozzle 50 and the hole 36' from contamination.

According to one variation, the cartridge may be a plastic syringe. The cartridge adapter and the micro nozzle 50 may in this case be placed in a moulding tool before injecting plastics to form the cartridge. The micro nozzle 50 and the cartridge adapter thereby become integral with the cartridge. A similar method is used when integrating RFID chips with plastic parts. The end product is generally similar to the assembly shown in FIGS. 2A-2C.

Figure 3A:
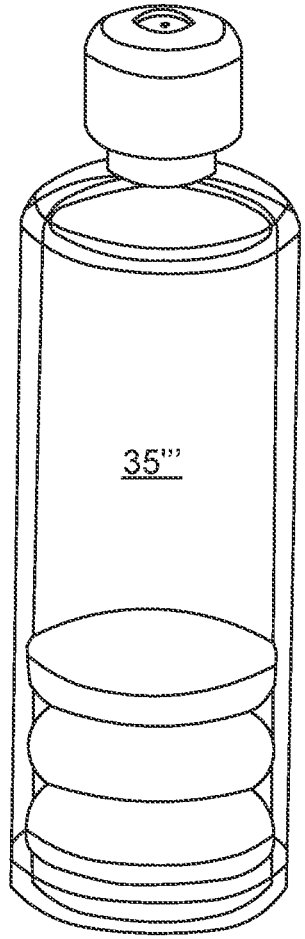
FIG. 3A is a perspective view of a cartridge comprising a crimp seal.
Figure 3B:
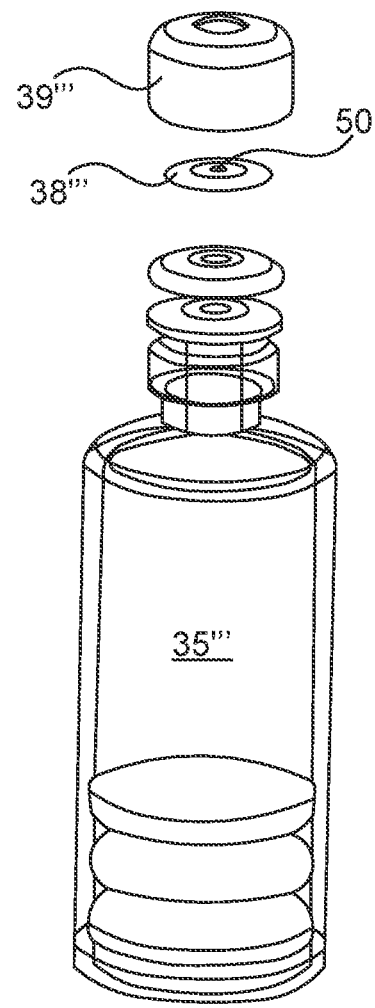
FIG. 3B is a perspective exploded view of the cartridge of FIG. 4A, the crimp seal comprising a cartridge adapter and micro nozzle.

Another example of an assembly for a spray device is shown in FIG. 3A and 3B. Crimp seal technology is used to attach the micro nozzle 50 to a cartridge 35'''. The cartridge adapter 38''', which for example may be a stainless steel carrier, is used to hold the micro nozzle 50. The spray device comprises a crimp seal 39'''. The crimp seal may for example be made of metal. The cartridge adapter 38''' and the micro nozzle 50 may be assembled with the crimp seal 39'''. The cartridge adapter 38''' and the micro nozzle 50 may be arranged between the cartridge 35' and the crimp seal 39'''. The cartridge adapter 38''' and the micro nozzle 50 may be arranged in the crimp seal 39'''. The micro nozzle 50 may be arranged adjacent to and aligned with an opening of the cartridge 35'''. The crimp seal 39''' is then crimped to an end of the cartridge 35''' when enclosing the micro nozzle 50 and the cartridge adapter 38'''. The cartridge 35''' may be filled with the liquid to be sprayed prior to the crimping of the crimp seal 39'''. The cartridge 35''' may beneficially be filled with the liquid in conjunction with the micro nozzle 50 being permanently attached to the cartridge 35'''. The cartridge 35''' may hence for example be filled just prior to the attachment of the micro nozzle 50 by crimping of the crimp seal 39'''.

The micro nozzle is permanently attached to the cartridge 35, 35', 35''' before or in conjunction with the filling of the cartridge 35, 35', 35'''. The micro nozzle 50 may be attached to the cartridge 35, 35', 35''' by means of any of the herein disclosed examples.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An assembly for a spray device, which assembly comprises:
   a cartridge containing a liquid to be pressurized, wherein the cartridge is a syringe provided with a hole,
   a micro nozzle configured to produce an aerosol from the pressurised liquid, wherein the micro nozzle is permanently attached to the syringe, and wherein the micro nozzle is positioned in the hole, and
   a cartridge adapter fixed to a tip of the syringe configured to hold the micro nozzle in position relative to the syringe, wherein the micro nozzle is mounted in the cartridge adapter.

2. The assembly according to claim 1, wherein the micro nozzle has a hexagonal shape which fits in the hole.

3. The assembly according to claim 1, wherein the micro nozzle is glued to the syringe.

4. The assembly according to claim 1, wherein the cartridge adapter is glued to the syringe.

5. The assembly according to claim 1, comprising a boot arranged on the tip of the syringe, configured to hermetically protect the hole and the micro nozzle from contamination.

6. The assembly according to claim 1, wherein the micro nozzle, the cartridge adapter, and the syringe are integrated by moulding.

7. The assembly according to claim 1 wherein the syringe is a medical cartridge.

8. The assembly according to claim 1, wherein the micro nozzle is press fit in the hole.

9. A method of assembling an assembly for a spray device, wherein the method comprises:

attaching a micro nozzle permanently to a tip of a cartridge via a cartridge adapter before or in conjunction with filling of the cartridge, wherein the cartridge is a syringe provided with a hole, wherein the micro nozzle is positioned in the hole, and wherein the micro nozzle is mounted in the cartridge adapter.

10. The method according to claim 9, comprising placing the cartridge adapter and the micro nozzle in a moulding tool, and injecting plastic to mould the syringe.

11. The method according to claim 9, wherein the micro nozzle has a hexagonal shape.

12. The method according to claim 9, wherein the attaching involves gluing of the micro nozzle.

13. The method according to claim 9, wherein the attaching involves press fitting the micro nozzle into the hole.

14. An assembly for a spray device, which assembly comprises:

a cartridge holder;

a cartridge containing a liquid, wherein the cartridge is configured to be pressurized, and a micro nozzle permanently attached to a tip of the cartridge adjacent a proximal end of the cartridge via a cartridge adapter, wherein the micro nozzle is operatively positioned within a hole located at the proximal end of the cartridge, wherein the micro nozzle is mounted in the cartridge adapter, and wherein the micro nozzle has an inlet orifice adjacent the proximal end of the cartridge and an outlet orifice in fluid communication with the inlet orifice such that when the cartridge is pressurized the liquid will flow through the inlet orifice and will exit the outlet orifice as an aerosol.

15. The assembly according to claim 14, wherein there are more inlet orifices than outlet orifices.

16. The assembly according to claim 14, further comprising a mouthpiece operatively connected to the cartridge holder.

17. The assembly according to claim 14, wherein the micro nozzle has a hexagonal shape.

18. The assembly according to claim 14, wherein the cartridge adapter is configured to hold the micro nozzle in position relative to the cartridge.

* * * * *